United States Patent [19]
Tan

[11] Patent Number: 5,227,570
[45] Date of Patent: Jul. 13, 1993

[54] PROCESS FOR SEPARATION OF ETHYLBENZENE OR ETHYLBENZENE/P-XYLENE FROM A XYLENE ISOMERS MIXTURE

[75] Inventor: Chung-Sung Tan, Hsinchu, Taiwan

[73] Assignee: Taiwan Styrene Monomer Corporation, Taipei, Taiwan

[21] Appl. No.: 801,531

[22] Filed: Dec. 2, 1991

[51] Int. Cl.$^5$ .............................................. C07C 7/12
[52] U.S. Cl. ..................................... 585/822; 585/828
[58] Field of Search ................................ 585/822, 828

[56] References Cited

U.S. PATENT DOCUMENTS

| | | | |
|---|---|---|---|
| 3,943,183 | 3/1976 | Rosback | 585/828 |
| 4,051,192 | 9/1977 | Neuzil et al. | 585/828 |
| 4,326,091 | 4/1982 | Maas et al. | 585/828 |
| 4,439,535 | 3/1984 | Smolin et al. | 502/62 |

OTHER PUBLICATIONS

Ello Santacesaria, et al., "Separation of Xylenes on Y Zeolites in the Vapor Phase. I. Determination of the Adsorption Equilibrium Parameters and of the Kinetic Regime", Ind. Eng. Chem. Process Des. Dev. 1985, 24, 78-83.

Chung-Sung Tan and Jeng-Leei Tsay. "Separation of Xylene Isomers on Silicalite in Supercritical and Gaseous Carbon Dioxide." Ind. Eng. Chem. Res. vol. 29, 502-504, 1990.

Primary Examiner—Anthony McFarlane
Assistant Examiner—Nhat D. Phan
Attorney, Agent, or Firm—Winstead Sechrest & Minick

[57] ABSTRACT

A process for separating ethylbenzene and p-xylene from a xylene isomers mixture, additional containing m-xylene and o-xylene, by selective adsorption of ethylbenzene and p-xylene on a silicalite absorbent is disclosed in the present invention, wherein a compressed gaseous $CO_2$ stream is used as a carrier for carrying a fixed amount of the mixture to the adsorbent bed for the selective adsorption, followed by a supercritical $CO_2$ stream desorption of the adsorbed ethylbenzene and p-xylene from the adsorbent bed. A method for recycling the $CO_2$ used therein is also disclosedby, which involves an isothermal and isobaric adsorption of the xylene isomer products from the effluent $CO_2$ streams.

18 Claims, 10 Drawing Sheets

PROCESS FOR SEPARATION OF ETHYLBENZENE OR ETHYLBENZENE/P-XYLENE FROM A XYLENE ISOMERS MIXTURE

FIELD OF THE INVENTION

The present invention is directed to the adsorptive separation of ethylbenzene or ethylbenzene/p-xylene from a xylene isomers mixture additional containing m-xylene and o-xylene, wherein silicalite is used as an adsorbent and $CO_2$ is used as a carrier or desorbent depending on its pressure.

BACKGROUND OF THE INVENTION

Xylene isomers are important industrial raw materials, which usually come from naphtha crackers and reformers as a mixture. The xylene isomers mixture contains meta-xylene (m-xylene, MX), ortho-xylene (o-xylene, OX), para-xylene (p-xylene, PX) and ethylbenzene (EB), wherein o-xylene can be used for synthesizing phthalic acid, m-xylene can be used for synthesizing isophthalic acid or can be converted to p-xylene which is an important raw material for manufacturing polyester fibers, and ethylbenzene can be used for producing styrene monomer. Because the xylene isomers have close boiling points, it is difficult to separate them by distillation. In the prior art, a cryogenic crystallization technique has been developed to separate the xylene isomers mixture comprising cooling the mixture until p-xylene being crystallized and separating the p-xylene crystals therefrom. This technique is relatively energy and capital intensive. Moreover, the recovery is limited to 73% of the feed due to the solid-liquid equilibrium.

In the present industrial practice the separation for xylene isomer mixture is usually achieved by the adsorption on zeolite adsorbents under liquid-phase or vapor-phase operation. Several patents dealing with this method are available, such as U.S. Pat. Nos. 3,943,183; 4,051,192; 4,326,091 and 4,439,535. With this method, the desorbent is generally required, and p-diethylbenzene, isopropylbenzene, propylbenzene, and toluene are the most employed desorbents. The desorbent used is recovered by distillation which is relatively energy intensive. A comprehensive introduction to this adsorptive separation can be found in the text book written by D. M. Ruthven, entitled "Principles of Adsorption and Adsorption Processes" John Wiley & Sons, New York (1984).

E. Sautacesaria et al. in their article entitled "Separation of Xylenes on Y Zeolites in the Vapor Phase. 1. Determination of the Adsorption Equilibrium Parameters and of the Kinetic Regime," Ind. Eng. Chem. Process Des. Dev. 24, 78–83 (1985) observed that separation could be improved by gas-phase operation and the quantity of desorbent used was relatively lower.

Chung-Sun Tan, the inventor of present invention, and Jeng-Leei Tsay in their article, entitled "Separation of Xylene Isomers on Silicalite in Supercritical and Gaseous Carbon Dioxide" Ind. Eng. Chem. Res., Vol. 29, 502–504, 1990, reported an experimental study of the separation of an equal amount of p- and m-xylenes on silicalite using carbon dioxide as the carrier. The results showed that the operations in the gaseous phase carbon dioxide offered a better separation efficiency over those at supercritical conditions. The effects of temperature, pressure and flow rate on the effectiveness of separation were also examined. It was found that, for a pulse of 1.0 cm$^3$ of xylene isomers and 39.5 g of silicalite, the most appropriate operating conditions were temperature around 85° C., pressure of 700 psia, and flow rate of 15.0 cm$^3$/min.

The object of present invention is to provide a process for separation of ethylbenzene or ethylbenzene/p-xylene from a xylene isomers mixture by selective adsorption on silicalite adsorbent, wherein a compressed gaseous $CO_2$ is used as a carrier and a supercritical $CO_2$ is used as a desorbent. As a result, the conventional desorbents are not used in the present process and thus the distillation separation for desorbents is prevented.

Another object of the present invention is to provide an integrated process for separation of ethylbenzene or ethylbenzene/p-xylene from a xylene isomers mixture by selective adsorption on silicalite adsorbent and recycling the $CO_2$ used therein, wherein the $CO_2$ is separated from the xylene products by an isothermal and isobaric selective adsorption separation and is recycled to the fresh $CO_2$ feed without additional heating and compressing.

SUMMARY OF THE INVENTION

A process for separation of ethylbenzene from a xylene isomers mixture, additionally containing at least one xylene isomer selected from the group consisting of m-xylene, o-xylene and p-xylene, comprising:

a) separating ethylbenzene from the mixture by selective adsorption of the ethylbenzene on a silicalite adsorbent bed, wherein a fixed amount of the mixture is introduced into the adsorbent bed by using a compressed high pressure gaseous $CO_2$ stream as a carrier, and a first stage effluent stream containing a xylene isomers composition having substantially no ethylbenzene is obtained from the adsorbent bed; and b) desorbing the adsorbed ethylbenzene from the adsorbent bed when the xylene isomers composition contained in the first stage effluent stream has a desired ethylbenzene percentage, wherein a supercritical $CO_2$ stream is fed to the adsorbent bed to obtain a second stage effluent stream containing a xylene isomers composition having substantially pure ethylbenzene.

The present invention also provides an integrated process for separating ethylbenzene from the xylene isomers mixture and recycling the $CO_2$ used therein, which comprises two additional steps following said a) and b):

a) separating ethylbenzene from the second stage effluent stream by selective adsorption of the ethylbenzene on a first activated carbon bed, wherein the second stage effluent stream is substantially isothermally and isobarically fed to the first activated carbon bed, and recycling a substantially pure $CO_2$ stream exiting from the first activated carbon bed to the supercritical $CO_2$ stream in step b); and d) separating the xylene isomers composition from the first stage effluent stream by selective adsorption of the sylene isomers composition on a second activated carbon bed, wherein the first stage effluent stream is substantially isothermally and isobarically fed to the second activated carbon bed, and recycling a substantially pure $CO_2$ stream exiting from the second activated carbon bed to the compressed high pressure gaseous $CO_2$ stream in step a).

Alternatively, the adsorption in step a) may be carried out to a less severe extent or for a shorter period, i.e. the desorption in step b) being initiated when the xylene isomers composition contained in the first stage effluent stream has a desired value of the sum of p-xylene and ethylbenzene percentages, whereby p-xylene and the ethylbenzene can be separated together from the xylene isomers mixture.

In the present process, the selective adsorption ability of the desired xylene isomer or isomers on the silicalite adsorbent is adjusted by changing gaseous $CO_2$ mobile phase to supercritical $CO_2$ fluid. As a result, a desorbent other than $CO_2$ is not required for the desorption in step b). Moreover, the $CO_2$ used can be separated from the xylene products by an isothermal and isobaric selective adsorption and recycled without additional heating and compressing, which overcomes the energy consumption problem involved in the conventional expansion-compression procedures for separating the $CO_2$-xylene effluent streams and recycling $CO_2$.

DETAILED DESCRIPTION OF THE INVENTION

The present invention provides a process for separating ethylbenzene alone or an ethylbenzene/p-xylene composition from a xylene isomers mixture additionally containing at least one xylene isomer selected from the group consisting of m-xylene, o-xylene and p-xylene. A fixed amount of the xylene isomers mixture is fed to a silicalite adsorbent bed by using a compressed high pressure gaseous $CO_2$ as a carrier, wherein the ethylbenzene or ethylbenzen/p-xylene are selective adsorbed from the mixture, and a first stage effluent stream is obtained from the adsorbent bed. The adsorbed ethylbenzene or ethylbenzene/p-xylene are desorbed from the adsorbent bed by a supercritical $CO_2$ purging when most of the xylene isomers other than ethylbenzene or ethylbenzene/p-xylene have been eluted from the adsorbent bed, so that a second stage effluent stream containing a xylene isomers composition having substantially pure ethylbenzene or ethylbenzene/p-xylene is obtained.

The xylene isomer products contained in the effluent streams can be easily recovered by vaporization of $CO_2$ by expansion; however, the vaporized $CO_2$ has to be recompressed for recycling to the adsorption or desorption stage, which is energy intensive. Therefore, the present invention also provides a process for selective adsorption of the xylene isomer products from the effluent streams and recycling the resulting $CO_2$, which comprises:

separating ethylbenzene or ethylbenzene/p-xylene products from the second stage effluent stream by selective adsorption of the products on a first activated carbon bed, wherein the second stage effluent stream is substantially isothermally and isobarically fed to the first activated carbon bed, and recycling a substantially pure $CO_2$ stream exiting from the first activated carbon bed to the supercritical $CO_2$; and separating xylene isomers from the first stage effluent stream by selective adsorption of the xylene isomers on a second activated carbon bed, wherein the first stage effluent stream is substantially isothermally and isobarically fed to the second activated carbon bed, and recycling a substantially pure $CO_2$ stream exiting from the second activated carbon bed to the compressed high pressure gaseous $CO_2$.

The xylene isomers mixture suitable for using in the present process preferably has a composition of 5-75 wt % ethylbenzene, 10-45 wt % m-xylene, 5-45 wt % o-xylene and 5-35 wt % p-xylene. Typically, they are produced and recovered from naphtha crackers or reformers and available in the petrochemical market. In one of the preferred embodiments of the present invention, a xylene isomers mixture having 54.55 wt % ethylbenzene, 26.43 wt % m-xylene, 10.10 wt % p-xylene and 8.92 wt % o-xylene was used. However, a xylene isomers mixture containing only two xylene isomers such as ethylbenzene/m-xylene or ethylbenzene/p-xylene is also suitable for the present separation process.

In the preferred embodiments of present invention, it was found that the silicalite adsorbent having a Si/Al ratio of 1040 has a better separation performance than that of 540. It is believed that the higher the Si/Al ratio the better the performance. Suitable silicalite for using in the present invention has a Si/Al ratio higher than 500, preferably higher than 1000. Basically, the silicalite adsorbent used in present process is not limited to any particular shapes or sizes; however, I find silicalite particles of mesh No. 24–32 have a better performance than silicalite pellets of 1.55 mm diameter and 6.2 mm length. Contemplated as the functional, or operative, equivalent of the silicalite adsorbent for the purpose of this invention are zeolites which can selectively adsorb ethylbenzene or ethylbenzene from the xylene isomers mixture in a compressed high pressure gaseous $CO_2$ mobile phase and the adsorbed ethylbenzene or ethylbenzene/p-xylene can be effectively desorbed by a supercritical $CO_2$ purging.

The compressed high pressure gaseous $CO_2$ has a temperature of 50°–120° C., preferably 70°–110° C., and a pressure of 500–800 psia, preferably 600–700 psia.

The supercritical $CO_2$ has a temperature of 50°–120° C., preferably 70°–110° C., and a pressure higher than 1070. It is known that the desorption will be completed within a shorter period of time if the pressure of supercritical $CO_2$ is increased; however, the higher the pressure the higher the operation and capital cost. In general, the pressure of supercritical $CO_2$ is within 1100–1600 psia, preferably 1200–1500 psia.

Both the first and second activated carbon beds contain a sufficient amount of activated carbon such that the xylene isomer products contained in the effluent streams can be completed adsorbed by the activated carbon beds for at least one operation cycle, preferably several operation cycles. The xylene isomer products adsorbed by the activated carbon can be recovered by any suitable regeneration techniques for loaded activated carbon known in the art, for example stram regeneration or supercritical regeneration method. Selectively, the substantially pure $CO_2$ stream exiting from the first activated carbon bed, instead of being recycled to the supercritical $CO_2$ stream, may be used for regenerating the second activated carbon bed.

The following examples are only used to illustrate the present invention and not meant to be limiting.

EXAMPLE 1

Separation of m-xylene (MX) and ethylbenzene (EB)

Figure 1:
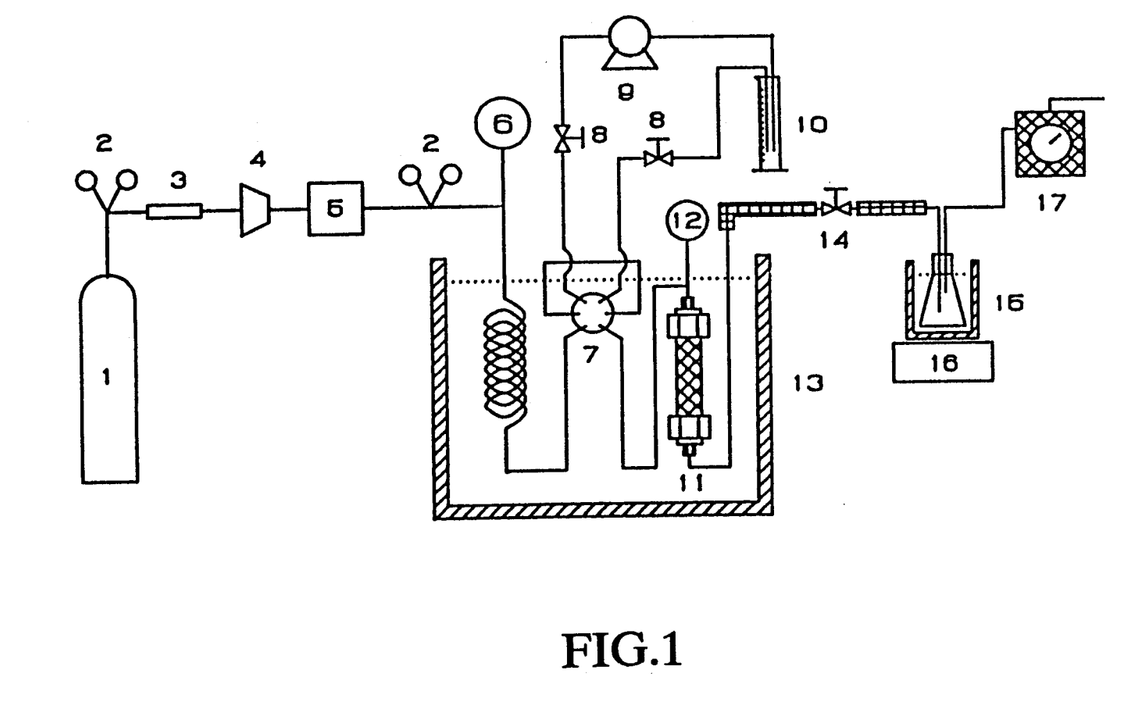
FIG. 1 is a schematic diagram of a process for adsorptive recovery of ethylbenzene or ethylbenzene/p-xylene from a xylene isomers mixture, wherein 1 is a $CO_2$ cylinder, 2 is a regulator, 3 is zeolite 4A, 4 is a compressor, 5 is a surge tank, 6 is a pressure gauge, 7 is a sampling valve, 8 is a needle valve, 9 is a tubing pump, 10 is a xylene mixture, 11 is a packed bed, 12 is a thermocouple, 13 is an oil bath, 14 is a metering valve, 15 is a cold trap, 16 is a magnetic stirrer and 17 is a wet gas meter.

The present example uses the separation system illustrated in FIG. 1 to separate a mixture having an equal amount of MX and EB.

Silicalite pellets having a diameter of 0.16 cm, a length of 0.62 cm and a Si/Al ratio of 1040 available from Union Carbide Corp. were used as adsorbent. Silicalite has a structure similar to ZSM-5 except the Al content of silicalite is significantly lower than that of ZSM-5. The physical properties of silicalite used are listed in the following Table 1.

TABLE 1

Surface area (BET) = 343.1 m²/g (<600A)
Pore volumn (N2) = 0.2553 cm³/g (<600A)
Pore volumn (Hg) = 0.3272 cm³/g (<37.5A–325 μm)
Bulk density = 0.7532 g/cm³
Particle density = 1.2025 g/cm³
True density = 1.9825 g/cm³
Bed voidage = 0.3736
Particle porosity = 0.3934

Before use, these pellets were dried at 120° C. for four hours and activated at 600° C. for 24 hours. About 39.5 g of silicalite pellets was weighed as soon as the temperature dropped to 120° C. and packed into a stainless steel 316 column of 2.12 i.d. and 25 cm length. In order to achieve an uniform flow distribution in the packed bed 11, glass beads of 0.1 cm diameter were packed above and below the silicalite packing to heights of about 6.3 and 5.3 cm, respectively.

A mixture prepared by mixing equal weight of research-grade EB and MX was fed to a six-port sampling valve 7 (Rheodyne) by a pump 9. The volumn of the sampling loop was 1.0 cm³. Carbon dioxide with a purity at least 99.7% was used as the carrier. It was first passed through a zeolite 4A bed 3 to remove any water vapor and hydrocarbons, and it was then compressed by a diaphram compressor 4 (Superpressure Inc.) and sent to a surge tank 5. In each experiments the pressure was maintained to within five psi of the desired value. The temperature was controlled in an oil bath 13 whose accuracy was about 0.5° C. A preheating coil was immersed in the bath to allow the fluid to reach the desired temperature.

Before injection of the mixture, the six-port sampling valve 7 was switched to let carbon dioxide bypass the sampling loop. When the flow rate of carbon dioxide reached a stable value, the six-port sampling valve 7 was switched to allow the carbon dioxide carrying the mixture to flow into the packed bed 11. The effluent fluid from the bed was expanded across a metering valve 14 and flowed through a cold trap 15 whose temperature was about −20° C. EB and MX were collected in the cold trap 15 which contained 1.0 L alcohol. Samples of 6.0 μL were frequently sent to a GC (Varian 3700) for compsoition analysis. The flow rate in the packed bed was determined by measuring the volumn of the gas with a wet test meter 17.

Figure 3:
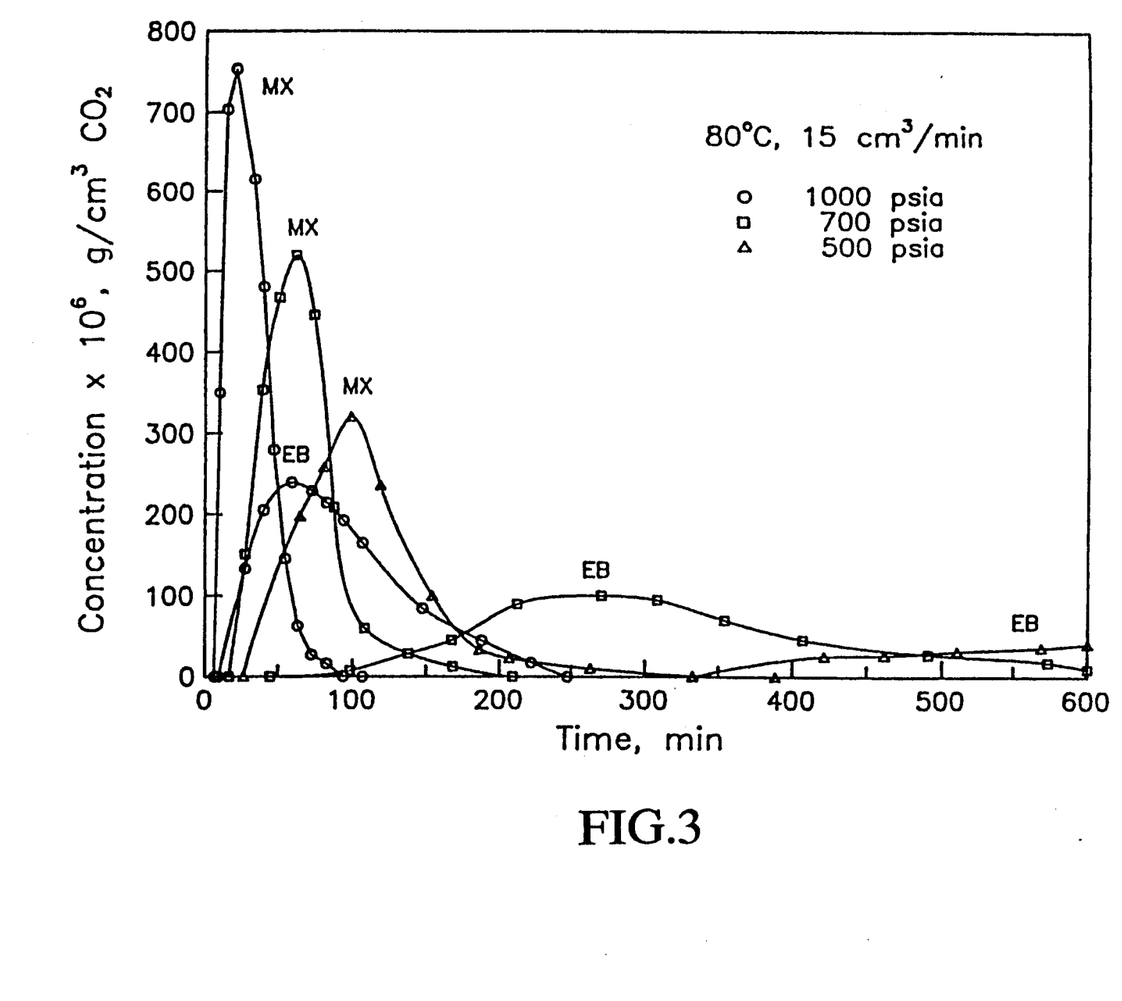
FIG. 3 is a plot showing the effect of pressure on the EB and MX adsorptive separation.
Figure 4:
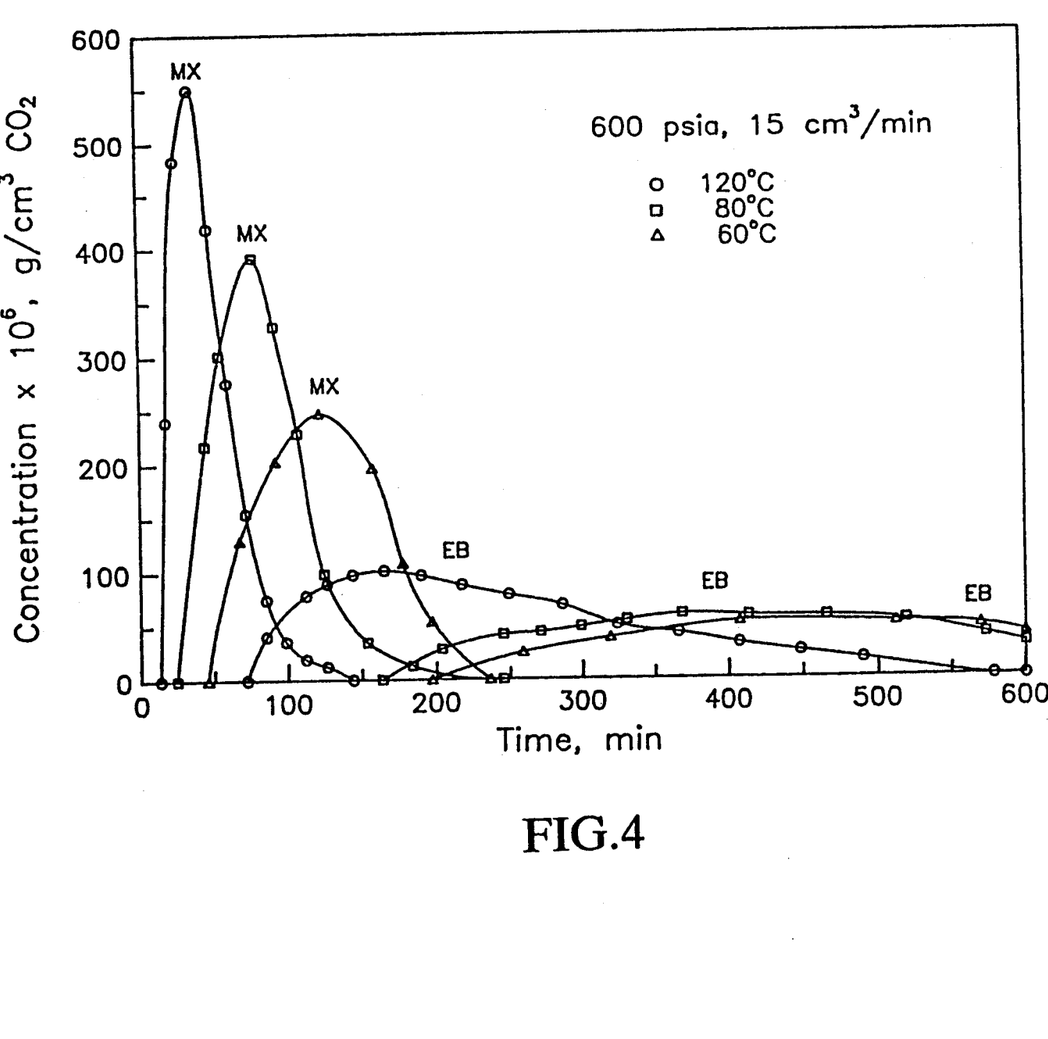
FIG. 4 is a plot showing the effect of temperature on the EB and MX adsorptive separation.
Figure 5:
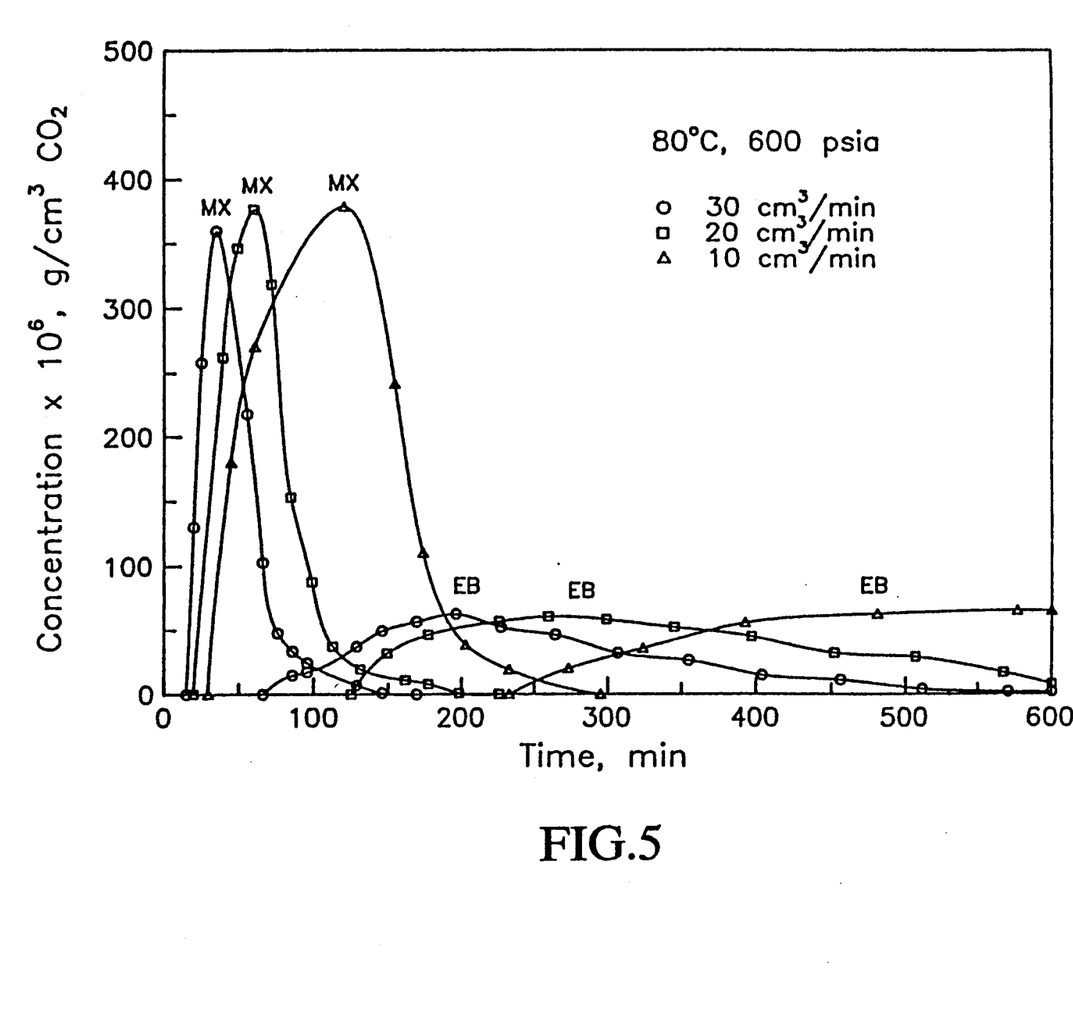
FIG. 5 is a plot showing the effect of flow rate on the EB and MX adsorptive separation.

The total amounts of EB and MX collected in the cold trap 15 were determined by measuring the final concentrations in the cold trap. These amounts were compared with those calculated by integrating the response curves. The agreements were satisfactory. The amounts collected were also found to be close to the injection amounts (deviation less than 5%). The results are shown in Table 2, and some typical results are also presented in FIGS. 3–5.

TABLE 2

| T (°C.) | P (psia) | $CO_2$ (cm³/min) | $t_{MX}$ (min) | $t_{EB}$ (min)[a] | Recovery MX (%) | Recovery EB (%) |
|---|---|---|---|---|---|---|
| Pressure Effect | | | | | | |
| 80 | 500 | 15.1 | 116 | 481(27%)[b] | 99.6 | 100.0 |
| 80 | 550 | 15.3 | 99 | 446(50%) | 99.4 | 100.0 |
| 80 | 600 | 14.8 | 86 | 391(73%) | 98.1 | 98.4 |
| 80 | 650 | 15.1 | 74 | 368(81%) | 95.5 | 94.8 |
| 80 | 700 | 15.2 | 59 | 264(98%) | 93.7 | 89.1 |
| 80 | 1000 | 15.3 | 28 | 89(100%) | 15.8 | 59.3 |
| 80 | 1200 | 15.4 | 16 | 40(100%) | 8.4 | 34.3 |
| Temperature Effect | | | | | | |
| 60 | 600 | 15.2 | 122 | 424(58%) | 96.8 | 96.6 |
| 70 | 600 | 15.1 | 112 | 432(63%) | 99.4 | 100.0 |
| 80 | 600 | 14.8 | 86 | 391(73%) | 98.1 | 98.4 |
| 90 | 600 | 15.3 | 80 | 396(67%) | 97.2 | 95.7 |
| 120 | 600 | 15.3 | 45 | 294(99%) | 93.1 | 85.2 |
| Flow Rate Effect | | | | | | |
| 80 | 600 | 10.0 | 117 | 441(44%) | 98.7 | 99.5 |
| 80 | 600 | 14.8 | 86 | 391(73%) | 98.1 | 98.4 |
| 80 | 600 | 20.4 | 68 | 333(92%) | 97.7 | 97.3 |
| 80 | 600 | 25.6 | 56 | 297(97%) | 97.5 | 96.6 |
| 80 | 600 | 30.1 | 47 | 250(98%) | 96.2 | 96.5 |
| Reproducibility Test | | | | | | |
| 80 | 600 | 14.8 | 86 | 391(73%) | 98.1 | 98.4 |
| 80 | 600 | 15.2 | 86 | 374(77%) | 98.0 | 97.9 |
| 80 | 650 | 15.1 | 82 | 370(65%) | 95.1 | 93.2 |
| 80 | 650 | 15.1 | 74 | 368(81%) | 95.5 | 94.8 |

[a] $t_{EB}$ was calculated with $t_o = 600$ min.
[b] The fraction of the injected amount was collected within 600 min.

The mean retention time in Table 2 is defined as $$\bar{t} = \int_0^{t_0} C \cdot t \, dt / \int_0^{t_0} C \, dt$$

wherein C is concentration, t is time. The recovery is defined as the amount collected with a purity higher than 98% over the total experimental period divided by the injected amount. A desirable separation process should possess less retention time and higher recovery.

It is obvious from Table 2 that a compromise between recovery and retention time exists. For example, with the temperature and the flow rate fixed at 80° C. and 15 cm³/min respectively, Table 2 and FIG. 3 indicate that at the pressure of 500 psia or 550 psia, the recoveries of both EB and MX are high. However, the operation time is relatively too long in comparison with that of 600 psia pressure. Considering both the recovery and operation time, it is found out that a pressure of about 600 psia, a temperature of about 80° C. and a flow rate of about 15 cm³/min are the more appropriate operation conditions.

Figure 6:
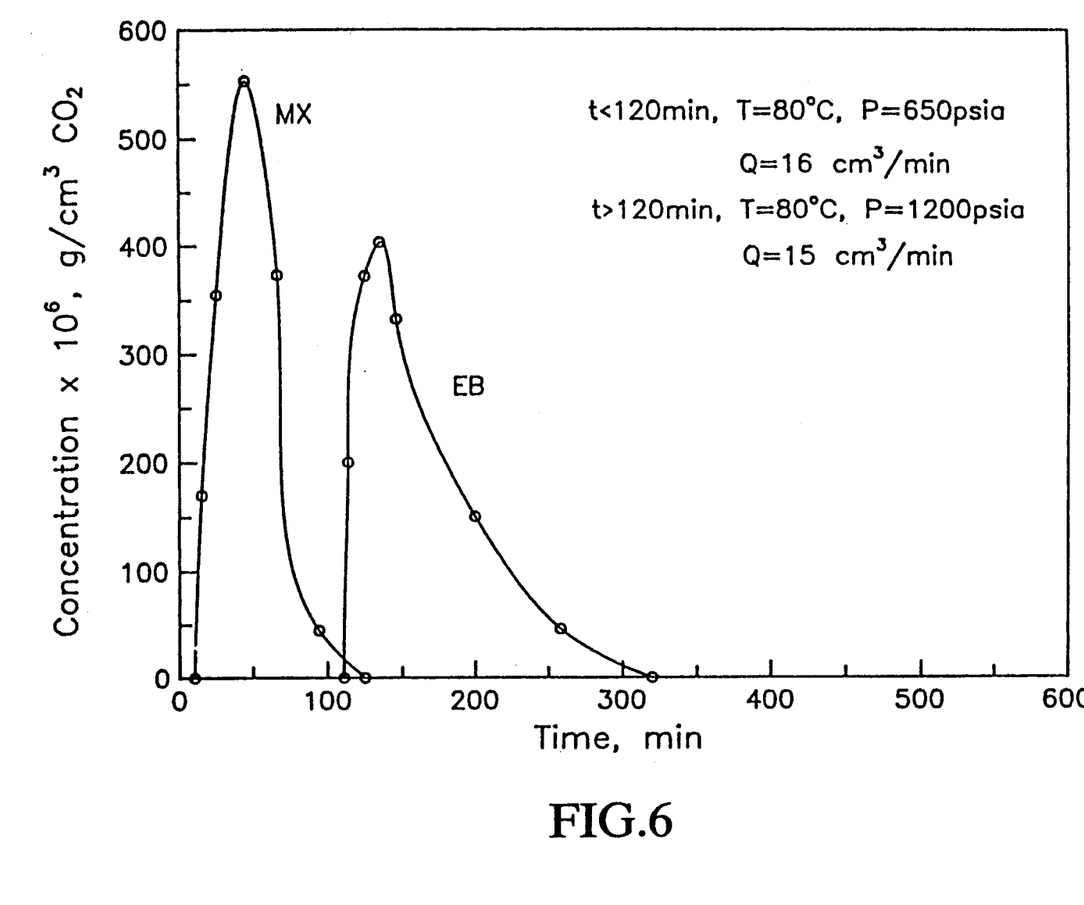
FIG. 6 is a plot showing EB and MX response curves in the adsorptive separation, wherein the pressure is increased from 650 psia to 1200 psia at separation time 120 minutes.

In order to further reduce the separation cycle time, it is suggested that the operation pressure is increased as most of the MX component is recovered from the effluent fluid such that the adsorbed EB can be desorbed from the silicalite more quickly. As shown in FIG. 6, the separation cycle time is reduced to about 330 minutes when the operation pressure is increased from 650 psia to 1200 psia at operation time 120 minutes.

EXAMPLE 2

Separation of p-xylene (PX) and ethylbenzene (EB)

The procedures of Example 1 were repeated except that a 0.5 ml mixture having equal weight of research-grade PX and EB was injected into the packed bed 11 instead of the MX/EB mixture. the results are shown in Table 3.

The data of Table 3 show that the operation conditions of 120° C. and 700 psia has a better separation. The recoveries of PX and EB under these operation conditions are 68.4% and 77.5%, respectively.

TABLE 3

| T (°C.) | P (psia) | CO₂ (cm³/min) | $\bar{t}_{PX}$ (min) | $\bar{t}_{EB}$ (min)$^a$ | Recovery PX (%) | EB (%) |
|---|---|---|---|---|---|---|
| Pressure Effect |||||||
| 80 | 550 | 15.0 | 426 | 523(20%)$^b$ | 54.9 | 84.2 |
| 80 | 600 | 15.7 | 326 | 451(35%) | 48.5 | 72.5 |
| 80 | 650 | 15.0 | 277 | 421(42%) | 40.1 | 71.7 |
| 80 | 700 | 14.5 | 227 | 409(55%) | 50.7 | 74.4 |
| Temperature Effect |||||||
| 80 | 700 | 14.5 | 229 | 409(55%) | 50.7 | 74.4 |
| 90 | 700 | 15.0 | 195 | 385(62%) | 47.7 | 75.5 |
| 100 | 700 | 15.4 | 162 | 358(65%) | 57.9 | 74.1 |
| 120 | 700 | 15.1 | 121 | 322(83%) | 68.4 | 77.5 |

$^{a,\,b}$The definitions are similar to Table 2.

EXAMPLE 3

Separation of 4-component Mixture

The procedures of Example 1 were repeated except that a mixture having 26.0 wt % m-xylene (MX), 8.8 wt % o-xylene (OX), 10.3 wt % p-xylene (PX) and 54.9 wt % ethylbenzene (EB) was used instead of the MX/EB mixture. The operation pressure was increased from 650 psia to 1200 psia at 120 minutes. The operation conditions and results are shown in FIG. 7.

Figure 7:
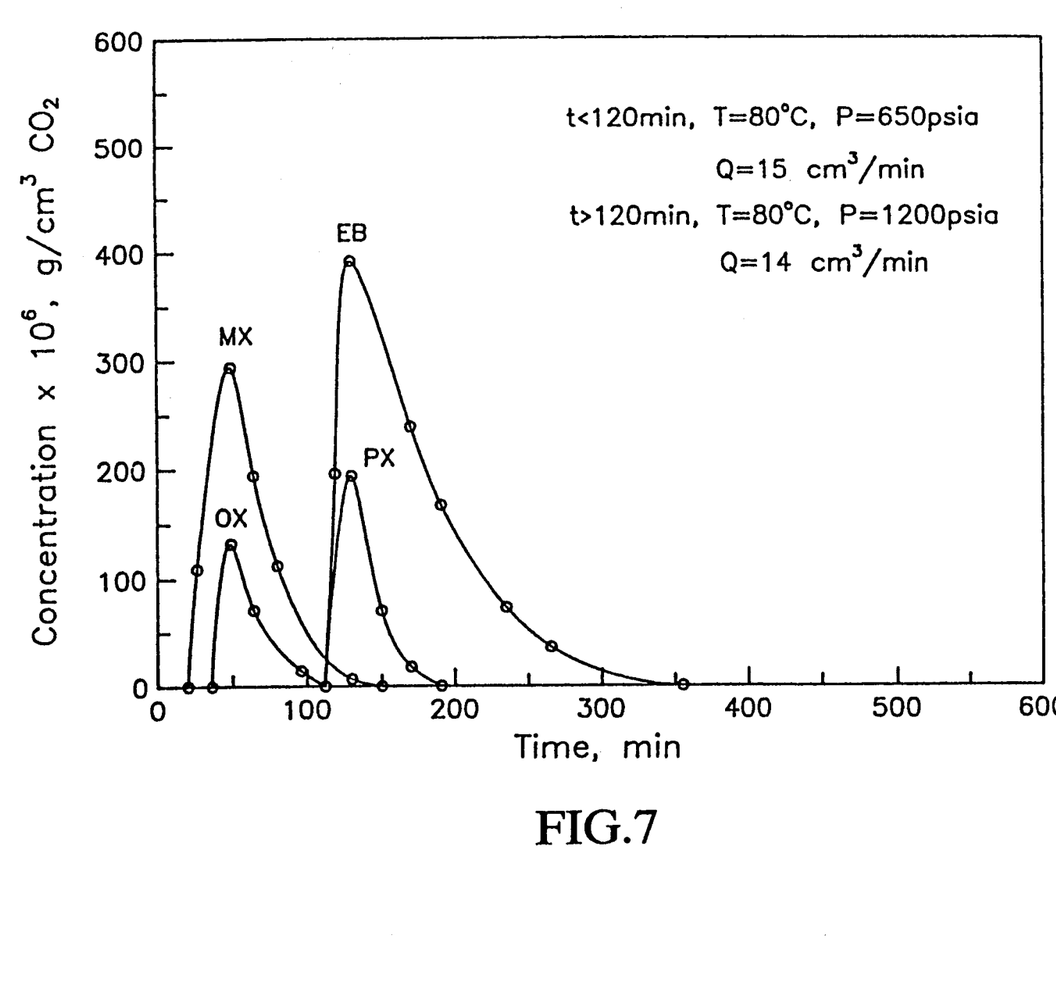
FIG. 7 is a plot showing EB, MX, PX and EB response curves in the adsorptive separation, wherein the pressure is increased from 650 psia to 1200 psia at separation time 120 minutes.

It can be seen from FIG. 7 that the separation cycle is completed within 350 minutes, the products collected in the cold trap 15 within the first 110 minutes is a mixture of MX and OX, followed by a mixture rich in EB and PX, and finally pure EB. The amount of the pure EB recovered in the last stage is 34 wt % of the injected EB. The total EB recovery may be improved if the mixture rich in EB and PX is further separated in accordance with the process of Example 2. Alternatively, the 4-component mixture can be first separated into two portions: one is riched in MX and OX, and the other is riched in EB and PX. The latter one is then further separated to recover substantially pure EB and substantially pure PX two components in accordance with the process of Example 2.

EXAMPLE 4

Separation of ethylbenxene (EB) from 4-component Mixture

The procedures of Example 1 were repeated except that a mixture having 26.43 wt % m-xylene (MX), 8.92 wt % o-xylene (OX), 10.10 wt % p-xylene (PX) and 54.55 wt % ethylbenzene (EB) was used instead of the MX/EB mixture, and the amount of silicalite used is 37.63 g. In the present example, the size of silicalite, and the operation conditions such as temperature, pressure, the degree of pressure increased and time to increase the pressure were varied for obtaining a better EB recovery. The silicalite used in Runs 1–7 are pellets having 0.16 cm diameter and 0.62 cm length, and Runs 8–10 use mesh No. 24–32 particles. The operation conditions and results are shown in Table 4.

TABLE 4

| Run. | T (°C.) | P (psia) | $S_t^c$ (min) | $S_p^d$ (psia) | Cycle Time$^e$ (min) | Recovery EB (%) | (min)$^f$ |
|---|---|---|---|---|---|---|---|
| 1 | 80 | 600 | 365 | 1500 | — | 77.9 | (345) |
| 2 | 80 | 650 | 305 | 1500 | — | 78.2 | (260) |
| 3 | 100 | 650 | 305 | 1500 | 360 | 79.5 | (218) |
| 4 | 100 | 650 | 200 | 1500 | 260 | 77.5 | (202) |
| 5 | 100 | 650 | 180 | 1500 | 250 | 53.4 | (192) |
| 6 | 100 | 650 | 200 | 1200 | 300 | 72.9 | (206) |
| 7 | 100 | 650 | 180 | 1200 | 290 | 69.1 | (191) |
| 8 | 80 | 650 | 325 | 1500 | 380 | 97.1 | (249) |
| 9 | 100 | 650 | 220 | 1500 | 280 | 96.9 | (213) |
| 10 | 100 | 650 | 200 | 1500 | 260 | 87.9 | (202) |

$^c S_t$ is the time when operation pressure is increased.
$^d S_p$ is the pressure being increased to.
$^e$The separation cycle time.
$^f$The time when the recovery of EB is started.

Figure 8:
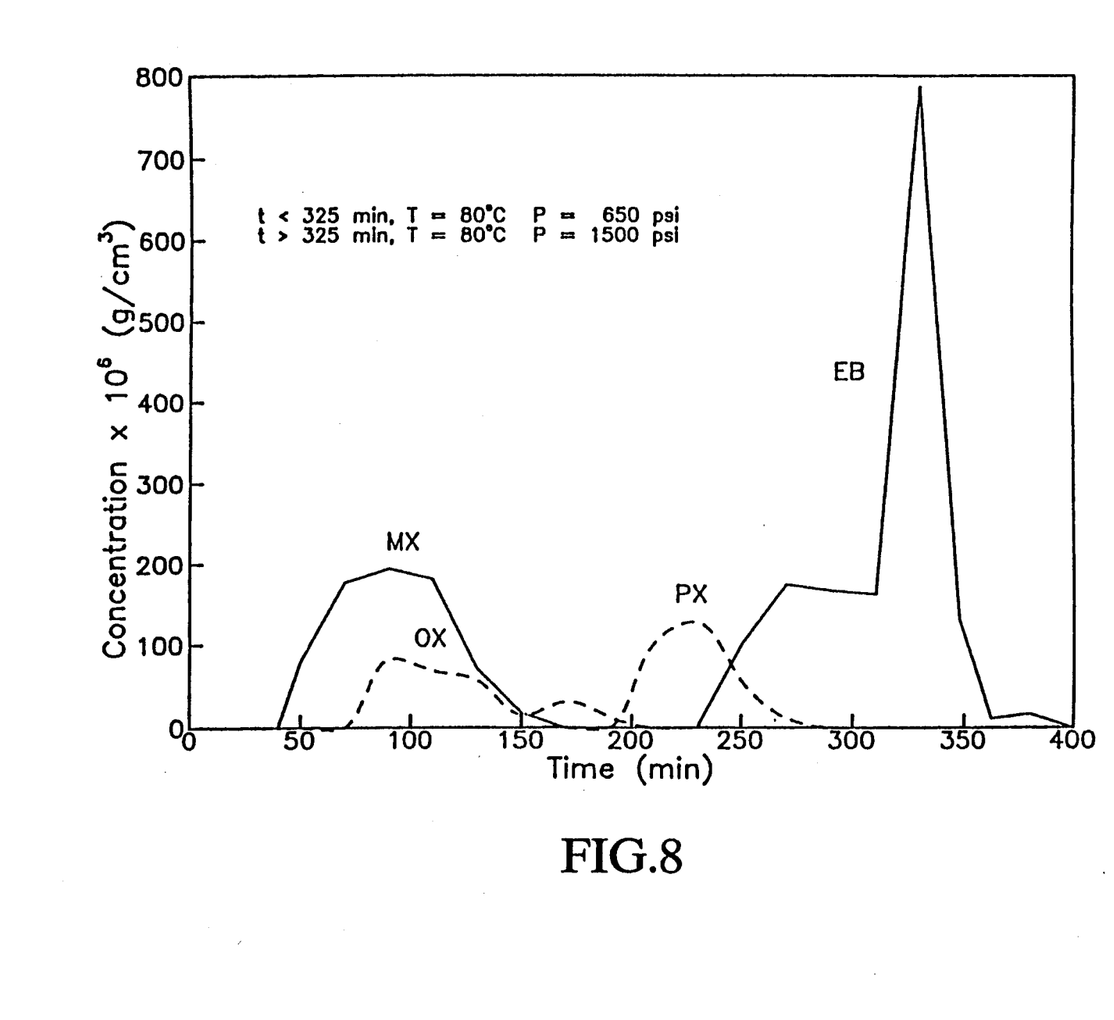
FIG. 8 is a plot showing EB, MX, PX and EB response curves in the adsorptive separation, wherein the pressure is increased from 650 psia to 1500 psia at separation time 325 minutes, and the silicalite used are particles of mesh No. 24-32.

The data of Table 4 show that the mesh No. 24–32 particles are better than the 0.16 cm × 0.62 cm pellets in the aspect of separation performance. Run 8 in Table 4 has the best EB recovery which is 0.2% higher than that of Run 9, but the separation cycle time thereof is significantly longer than that of Run 9. Therefore, Run 9 is preferred in view of the recovery and the operation cycle time. FIG. 8 shows the response curves of Run 8.

EXAMPLE 5

Recovering xylene products from the effluent fluid by activated carbon adsorption The purpose of present example is to illustrate that the xylene isomers contained in the effluent fluid from the adsorbent packed bed can be recovered by isothermal and isobaric activated carbon adsorption, whereby substantially pure CO₂ effluents from the activated carbon can be recycled to the silicalite adsorption/desorption without substantially heating or compressing.

Figure 9:
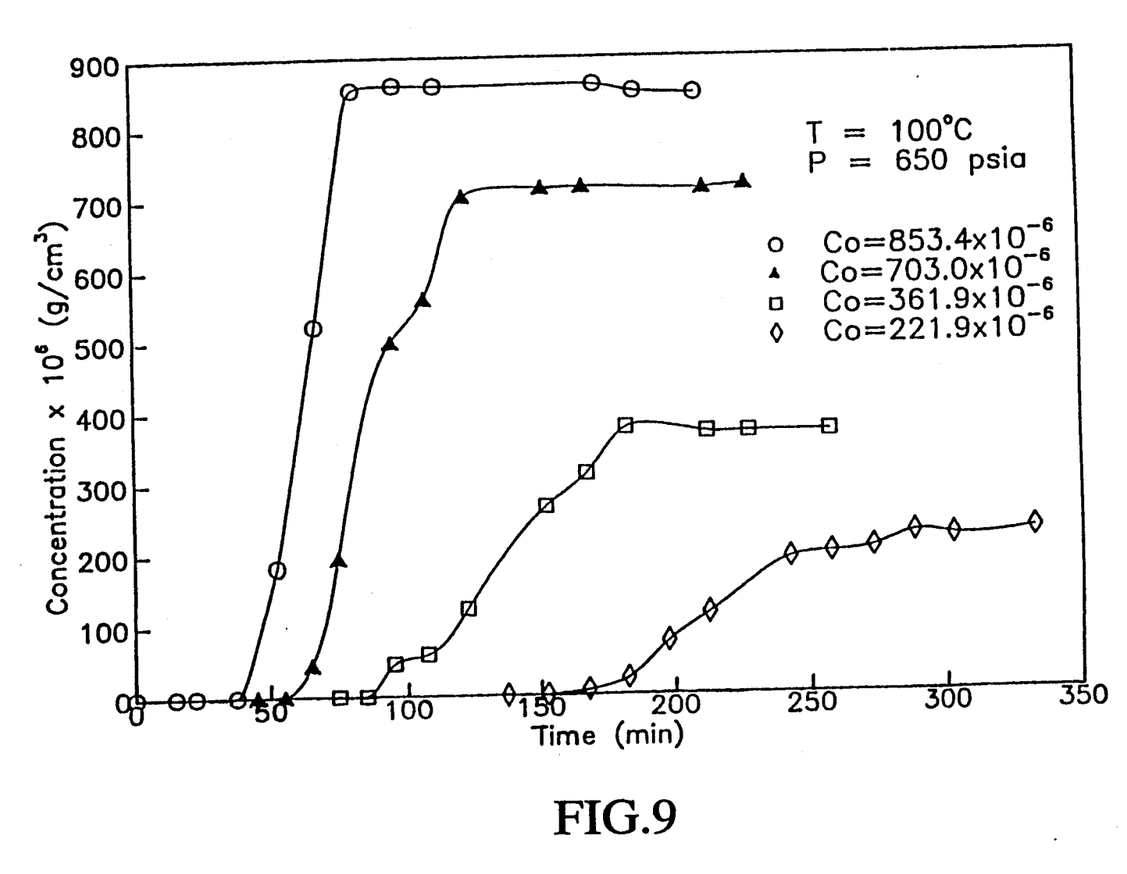
FIG. 9 is a plot showing the breakthrough curves in the adsorptive separation on activated carbon for $CO_2$ streams containing various MX concentrations, wherein the pressure is 650 psia and the temperature is 100° C.
Figure 10:
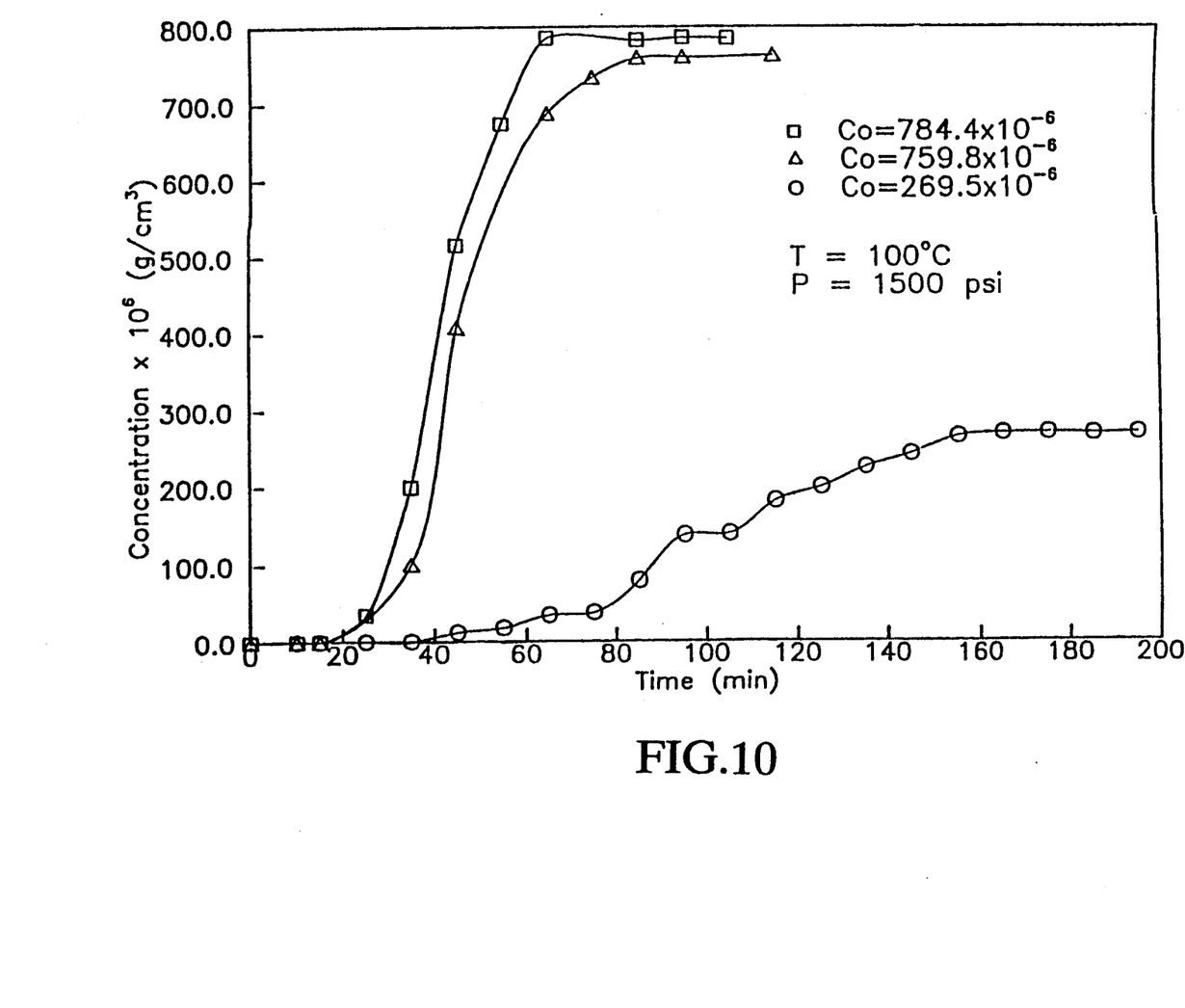
FIG. 10 is a plot showing the breakthrough curves in the adsorptive separation on activated carbon for $CO_2$ streams containing various EB concentrations, wherein the pressure is 1500 psia and the temperature is 100° C.

6 g of mesh No. 8–10 activated carbon particles were used to adsorb m-xylene from $CO_2$ streams having various m-xylene concentrations. The temperature, pressure and flow rate of the $CO_2$ streams are 100° C., 650 psia and 15 cm$^3$/min, respectively. The breakthrough curves are shown in FIG. 9. Similar experiments were run for ethylbenzene containing $CO_2$ streams. FIG. 10 shows the breakthrough curves of $CO_2$ streams having different concentrations of ethylbenzene at 100° C., 1500 psia and $CO_2$ flow rate 14 cm$^3$/min.

As it can be seen from FIG. 9, the MX is no longer adsorbed by the 6 g activated carbon at about 150 minutes for the $CO_2$ stream containing $221.9 \times 10^{-6}$ g/ml MX. It is known from FIG. 8 that the $CO_2$ effluent from the packed bed 11 has a maximun MX concentration of $200 \times 10^{-6}$ g/ml and the effluent time is about 250 minutes. Therefore, if the amount of activated carbon used is increased to 10 g or more, the MX/OX/PX isomers contained in the effluent within the first 250 minutes of FIG. 8 can be fully adsorbed at isothermal and isobarical condition.

As it can be seen from FIG. 10, the EB is no longer adsorbed by the 6 g activated carbon at about 15 minutes for the EB concentration $784 \times 10^{-6}$ curve. Similarly, the EB isomer contained in the last 130 minutes effluent of FIG. 8 can be adsorbed isothermally and isobarically by 54 g or more activated carbon.

EXAMPLE 6

Figure 2:
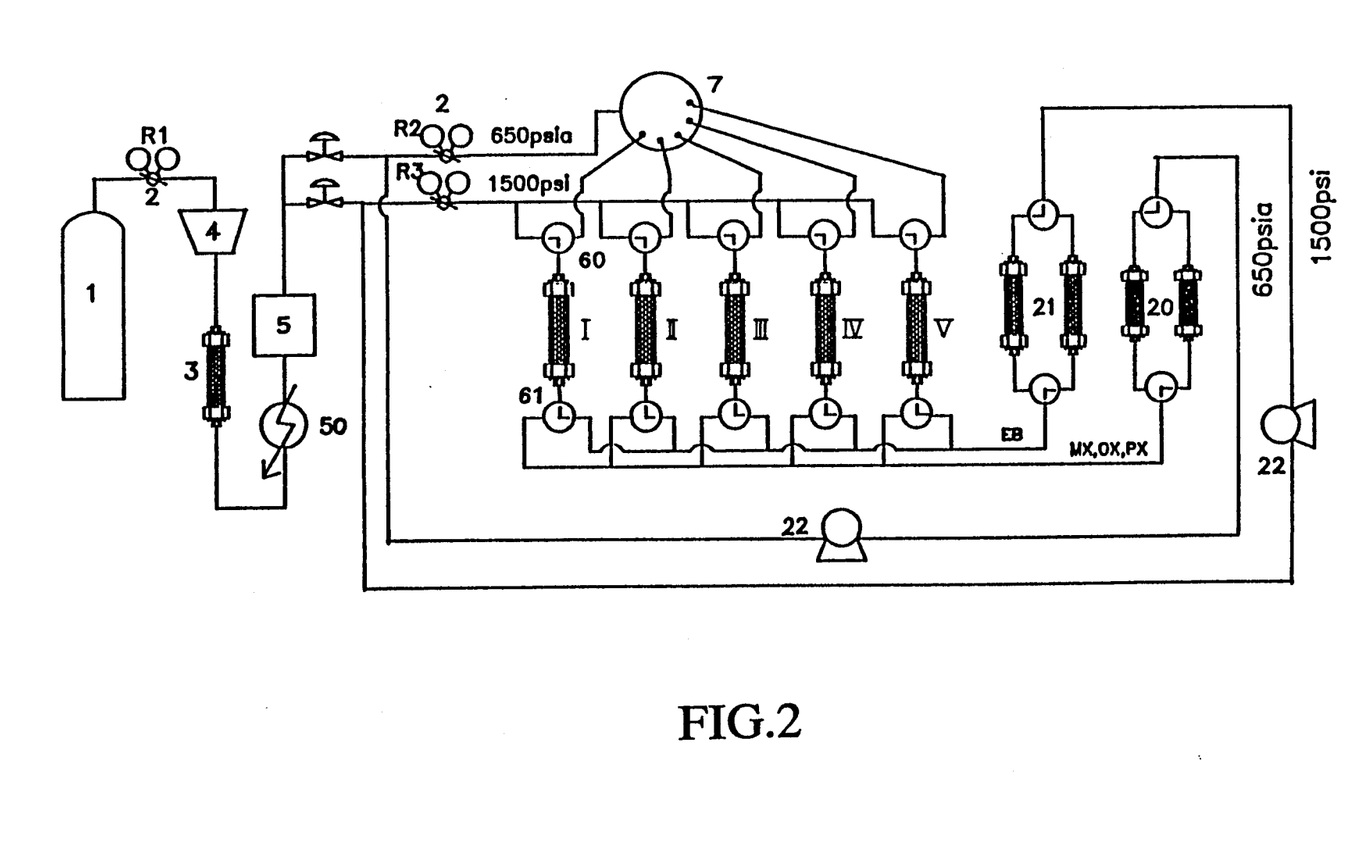
FIG. 2 is a schematic diagram of an integrated process for adsorptive recovery of ethylbenzene or ethylbenzene/p-xylene from a xylene isomers mixture followed by recovery of $CO_2$ by selective adsorption and recycle of the resulting $CO_2$, wherein I-V are fixed beds; R1, R2 and R3 are regulators; 20 and 21 are activated carbon beds; 22 is a metering pump; 50 is a heat-exchanger; 60 and 61 are three way valves. Similar features of this process utilize common numbering with FIG. 1.

An Integrated Process for Separating Xylene Isomers and Recycling $CO_2$ Used Therein A system illustrated in FIG. 2 was used to separate EB from xylene isomers, wherein the $CO_2$ used was recycled.

Referring to FIG. 2, $CO_2$ was first compressed and heated to 2500 psia and 100° C. by a compressor 4 and a heat-exchanger 5, respectively, which was then stored in a surge tank 5. The pressures of $CO_2$ was regulated to desired values by the regulators R2 and R3, and the flow rates of the $CO_2$ were controlled at 15 cm$^3$/min by the metering pumps 22. The mixture of xylene isomers were sequentially injected into the fixed beds I–V by switching the three way valves 60 to the sampling valve 7 which was connected to 650 psia $CO_2$ pipeline. The injections of xylene isomers mixture were carried out at an interval of 50 minutes. Before injection, the three way valve 61 at the bottom of the fixed beds were switched to the MX/OX/PX activated carbon bed 20. For each fixed beds I–V, the 650 psia $CO_2$ streams were introduced for 200 minutes, and then switched the three way valves 60 at the top of the fixed beds to the 1500 psia $CO_2$ pipeline and the three way valves 61 to the EB activated carbon bed 21 for additional 50 minutes. At this time the 650 psia recycled $CO_2$ stream was shifted to another fixed bed which required the injection of xylene isomers mixture. For example, at operation time of 200 minutes the 650 psia recycled $CO_2$ stream which originally recycled to the fixed bed I was shifted to recycle to the fixed bed V. As it can be seen from Table 5, the present process can be run continuously by using the system illustrated in FIG. 2.

The activated carbon bed 20 were packed into two separate columns. The two columns both contained a sufficient amount of activated carbon for at least several cycles of operation and were used one at a time. Accordingly, one can use the second column when the first column is regenerated without stopping the process. Similar design was adopted for the activated carbon bed 21.

TABLE 5

| Operation Sequences for a System Containing Five Fixed Beds | | | |
|---|---|---|---|
| | | the Course of Operation (min) | |
| Operation Step | Fixed Bed | Feeding @ | Adsorption End @ | Desorption End @ |
| 1 | I | 0 | 200 | 250 |
| 2 | II | 50 | 250 | 300 |
| 3 | III | 100 | 300 | 350 |
| 4 | IV | 150 | 350 | 400 |
| 5 | V | 200 | 400 | 450 |
| | | *the $CO_2$ carrier stream used is the one originally recycled to the fixed bed I whose pressure is increased from 650 to 1500 psia | | |
| 6 | I | 250 | 450 | 500 |
| | | *the $CO_2$ carrier stream used is the one originally recycled to the fixed bed II whose pressure is increased from 650 to 1500 psia | | |
| 7 | II | 300 | 500 | 550 |
| | | *the $CO_2$ carrier stream used is the one originally recycled to the fixed bed III whose pressure is increased from 650 to 1500 psia | | |
| 8 | III | 350 | 550 | 600 |
| | | *the $CO_2$ carrier stream used is the one originally recycled to the fixed bed IV whose pressure is increased from 650 to 1500 psia | | |
| 9 | IV | 400 | 600 | 650 |
| | | *the $CO_2$ carrier stream used is the one originally recycled to the fixed bed V whose pressure is increased from 650 to 1500 psia | | |
| 10 | V | 450 | 650 | 700 |
| | | *the $CO_2$ carrier stream used is the one originally recycled to the fixed bed I whose pressure is increased from 650 to 1500 psia | | |

What is claimed is:

1. A process for separating ethylbenzene from a xylene isomers mixture comprising:
    a) separating ethylbenzene from the mixture by selective adsorption of the ethylbenzene on a silicalite absorbent bed, wherein a fixed amount of the mixture is introduced into the adsorbent bed by using a compressed high pressure gaseous $CO_2$ stream, having a pressure of higher than about 500 psia, as a carrier, and a first stage effluent stream containing a xylene isomers composition having substantially no ethylbenzene is obtained from the adsorbent bed; and
    b) desorbing the adsorbed ethylbenzene from the adsorbent bed when the xylene isomers composition contained in the first stage effluent stream has a desired ethylbenzene percentage, wherein a supercritical $CO_2$ stream as a desorbent is fed to the adsorbent bed to obtain a second stage effluent stream containing a xylene isomers composition having substantially pure ethylbenzene.

2. The process of claim 1 wherein the desired ethylbenzene percentage in the step b) is 98wt %.

3. The process of claim 1 wherein the xylene isomers mixture contains ethylbenzene, m-xylene, o-xylene and p-xylene.

4. The process of claim 3 wherein the xylene isomers mixture has a composition of 5–75 wt % ethylbenzene, 10–45 wt % m-xylene, 5–45 wt % o-xylene and 5–35 wt % p-xylene.

5. The process of claim 1 wherein the xylene isomers mixture contains ethylbenzene and p-xylene.

6. An integrated process for separating ethylbenzene from a xylene isomers mixture and recycling $CO_2$ used therein comprising:
   a) separating ethylbenzene from the mixture by selective adsorption of the ethylbenzene on a silicalite adsorbent bed, wherein a fixed amount of the mixture is introduced into the adsorbent bed by using a compressed high pressure gaseous $CO_2$ stream, having a pressure of higher than about 500 psia, as a carrier, and a first stage effluent stream containing a xylene isomers composition having substantially no ethylbenzene is obtained from the adsorbent bed;
   b) desorbing the a adsorbed ethylbenzene from the adsorbent bed when the xylene isomers composition contained in the first stage effluent stream has a desired ethylbenzene percentage, wherein a supercritical $CO_2$ stream as a desorbent is fed to the adsorbent bed to obtain a second stage effluent stream containing a xylene isomers composition having substantially pure ethylbenzene;
   c) separating ethylbenzene from the second stage effluent stream by selective adsorption of the ethylbenzene on a first activated carbon bed, wherein the second stage effluent stream is substantially isothermally and isobarically fed to the first activated carbon bed, and recycling a substantially pure $CO_2$ stream existing from the first activated carbon bed to the supercritical $CO_2$ stream in step (b); and
   d) separating the xylene isomers composition from the first stage effluent stream by selective adsorption of the xylene isomers composition on a second activated carbon bed, wherein the first stage effluent stream is substantially isothermally and isobarically fed to the second activated carbon bed, and recycling a substantially pure $CO_2$ stream exiting from the second activated carbon bed to the compressed high pressure gaseous $CO_2$ stream in step a).

7. The process of claim 6 wherein the desired ethylbenzene percentage in the step b) is 98 wt %.

8. The process of claim 6 wherein the xylene isomers mixture contains ethylbenzene, m-xylene, o-xylene and p-xylene.

9. The process of claim 8 wherein the xylene isomers mixture has a composition of 5-75 wt % ethylbenzene, 10-45 wt % m-xylene, 5-45 wt % o-xylene and 5-35 wt % p-xylene.

10. The process of claim 6 wherein the xylene isomers mixture contains ethylbenzene and p-xylene.

11. A process for separating ethylbenzene and p-xylene from a xylene isomers mixture comprising:
   a) separating ethylbenzene and p-xylene from the mixture by selective adsorption of the ethylbenzene and p-xylene on a silicalite adsorbent bed, wherein a fixed amount of the mixture is introduced into the adsorbent bed by using a compressed high pressure gaseous $CO_2$ stream, having a pressure of higher than about 500 psia, as a carrier, and a first stage effluent stream containing a xylene isomers composition having substantially no ethylbenzene and no p-xylene is obtained from the adsorbent bed; and
   b) desorbing the adsorbed ethylbenzene and p-xylene from the adsorbent bed when the xylene isomers composition contained in the first stage effluent stream has a desired value of the sum of ethylbenzene and p-xylene percentages, wherein a supercritical $CO_2$ stream as a desorbent is fed to the adsorbent bed to obtain a second stage effluent stream containing a xylene isomers composition substantially having ethylbenzene and p-xylene.

12. The process of claim 11 wherein the desired value of the sum of ethylbenzene and p-xylene percentages in the step b) is 98 wt %.

13. The process of claim 11 wherein the xylene isomers mixture contains ethylbenzene, m-xylene, o-xylene and p-xylene.

14. The process of claim 13 wherein the xylene isomers mixture has a composition of 5-75 wt % ethylbenzene, 10-45 wt % m-xylene, 5-45 wt % o-xylene and 5-35 wt % p-xylene.

15. An integrated process for separating ethylbenzene and p-xylene from a xylene isomers mixture and recycling $CO_2$ used therein comprising:
   a) separating ethylbenzene and p-xylene from the mixture by selective adsorption of the ethylbenzene and p-xylene on a silicalite adsorbent bed, wherein a fixed amount of the mixture is introduced into the adsorbent bed by using a compressed high pressure gaseous $CO_2$ stream, having a pressure of higher than about 500 psia, as a carrier, and a first stage effluent stream containing a xylene isomers composition having substantially no ethylbenzene and no p-xylene is obtained from the adsorbent bed;
   b) desorbing the adsorbed ethylbenzene and p-xylene from the adsorbent bed when the xylene isomers composition contained in the first stage effluent stream has a desired value of the sum of ethylbenzene and p-xylene percentages, wherein a supercritical $CO_2$ stream as a desorbent is fed to the adsorbent bed to obtain a second stage effluent stream containing a xylene isomers composition substantially having ethylbenzene and p-xylene;
   c) separating ethylbenzene and p-xylene from the second stage effluent stream by selective adsorption of the ethylbenzene and p-xylene on a first activated carbon bed, wherein the second stage effluent stream is substantially isothermally and isobarically fed to the first activated carbon bed, and recycling a substantially pure $CO_2$ stream exiting from the first activated carbon bed to the supercritical $CO_2$ stream in step b); and
   d) separating the xylene isomers composition from the first stage effluent stream by selective adsorption of the xylene isomers composition on a second activated carbon bed, wherein the first stage effluent stream is substantially isothermally and isobarically fed to the second activated carbon bed, and recycling a substantially pure $CO_2$ stream exiting from the second activated carbon bed to the compressed high pressure gaseous $CO_2$ stream in step a).

16. The process of claim 15 wherein the desired value of the sum of ethylbenzene and p-xylene percentages in the step b) is 98 wt %.

17. The process of claim 15 wherein the xylene isomers mixture contains ethylbenzene, m-xylene, o-xylene and p-xylene.

18. The process of claim 17 wherein the xylene isomers mixture has a composition of 5-75 wt % ethylbenzene, 10-45 wt % m-xylene, 5-45 wt % o-xylene and 5-35 wt % p-xylene.

* * * * *

UNITED STATES PATENT AND TRADEMARK OFFICE
CERTIFICATE OF CORRECTION

PATENT NO. : 5,227,570
DATED : July 13, 1993
INVENTOR(S) : Chung-Sung Tan

It is certified that error appears in the above-indentified patent and that said Letters Patent is hereby corrected as shown below:

Col. 2, line 50, delete "a)" and insert -- c) --.

Col. 2, line 60, delete "sylene" and insert -- xylene --.

Col. 5, line 31, delete "stram" and insert -- steam --.

Col. 6, line 28, delete "compsoition" and insert -- composition --.

Col. 11, line 16, delete "the a adsorbed" and insert -- the adsorbed --.

Signed and Sealed this

Twenty-third Day of January, 1996

Attest:

BRUCE LEHMAN

*Attesting Officer*      *Commissioner of Patents and Trademarks*